United States Patent
Galon et al.

(10) Patent No.: US 9,645,152 B2
(45) Date of Patent: May 9, 2017

(54) METHODS FOR PREDICTING THE SURVIVAL TIME OF A PATIENT SUFFERING FROM A SOLID CANCER

(71) Applicants: Jerome Galon, Paris (FR); Franck Pages, Paris (FR); Herve Fridman, Paris (FR); Bernhard Mlecnik, Paris (FR)

(72) Inventors: Jerome Galon, Paris (FR); Franck Pages, Paris (FR); Herve Fridman, Paris (FR); Bernhard Mlecnik, Paris (FR)

(73) Assignees: Institut National de la Sante et de la Recherche Medicale (INSERM), Paris (FR); Universite Paris Descartes—Paris V, Paris (FR); Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 14/837,271

(22) Filed: Aug. 27, 2015

(65) Prior Publication Data
US 2015/0369811 A1    Dec. 24, 2015

Related U.S. Application Data

(63) Continuation of application No. 13/368,404, filed on Feb. 8, 2012, now abandoned.

(51) Int. Cl.
*G01N 1/30* (2006.01)
*G01N 33/574* (2006.01)

(52) U.S. Cl.
CPC ..... *G01N 33/57496* (2013.01); *G01N 33/574* (2013.01); *G01N 33/57419* (2013.01); *G01N 2333/54* (2013.01); *G01N 2800/52* (2013.01)

(58) Field of Classification Search
None
See application file for complete search history.

(56) References Cited

U.S. PATENT DOCUMENTS

2011/0008795 A1    1/2011   Ikeda et al.

FOREIGN PATENT DOCUMENTS

| WO | 2007/045996 | 4/2007 |
|----|-------------|--------|
| WO | 2012/038068 | 3/2012 |

OTHER PUBLICATIONS

Lim et al (Journal of Immunology, 2008, vol. 180, pp. 122-129).*
Kim et al (Journal of Clinical Investigation, 2001, vol. 107, pp. 595-601).*
Kryczek et al (Journal of Immunology, 2007, vol. 178, pp. 6730-6733).*
Tosolini, M., et al., "Clinical Impact of Different Classes of Infiltrating T Cytotoxic and Helper Cells (TH1, th2, treg, th17) in Patients with Colorectal Cancer", Cancer Reseach, 2011 Fef 15;71(4) : 1263-71. Epub Feb. 8, 2011. Inserm, Integrative Cancer Immunology Team, INSERM U872, Paris, France. Erratum in Cancer Res. Jul. 2011;71(13):4732.

* cited by examiner

*Primary Examiner* — Karen Canella
(74) *Attorney, Agent, or Firm* — Whitham, Curtis & Cook (57) ABSTRACT

The present invention provides methods and kits for the prognosis of survival time of a patient suffering from a cancerous tumor. The method involves quantitating the density of Th17 cells at the center of the tumor and at the invasive margin of the tumor, where low density values at each location indicate a favourable prognosis, high values at each location indicate an unfavourable prognosis, and heterogeneous values at the two locations (one high, one low) indicate an intermediate prognosis.

30 Claims, 5 Drawing Sheets

Figure 3B

METHODS FOR PREDICTING THE SURVIVAL TIME OF A PATIENT SUFFERING FROM A SOLID CANCER

CROSS-REFERENCE TO RELATED APPLICATIONS

This application is a continuation application of U.S. Ser. No. 13/368,404 filed Feb. 8, 2012.

FIELD OF THE INVENTION

The present invention relates to methods and kits for the prognosis of survival time of a patient suffering from a solid cancer. In particular, the invention provides methods involving the quantitation of Th17 cells in solid tumors as an indicator of the prognosis of survival time.

BACKGROUND OF THE INVENTION

Cancer progression is a complex process involving host-tumor interactions through multiple molecular and cellular factors of the tumor microenvironment. In mice, the immune cells appear to prevent the development of tumors and inhibit tumor progression (1). However, through inflammation-dependent mechanisms, the innate immune system can promote tumor development (2, 3). In humans, lymphocytes have been shown to participate in antitumoral responses. Tumor-infiltrating T cells are associated with improved clinical outcome and survival in colorectal cancer patients (4). Similar results were found in breast (5, 6) and lung cancer (7-11).

It was previously shown that a high intratumoral memory T cell density correlated with the decrease of early metastatic events and the prevention of relapse in colorectal cancer patients (12). Furthermore, it was demonstrated that the functional orientation, density and location of immune cells profoundly influence the clinical outcome of patients, regardless of cancer stages (4). In contrast to patients with metastasis or a low density of immune cells, a functional coordination of the immune response was observed in patients without metastasis and with a high density of immune cells (13).

SUMMARY OF THE INVENTION

For the present invention, the aim of the inventors was to analyze the balance between the densities of cytotoxic T cells and different subsets of helper T-cells in cancers involving solid tumors (e.g. colorectal cancer), and to elucidate the impact of cell densities on disease-free survival of cancer patients. The tumor microenvironment was thus investigated in 125 frozen colorectal tumor samples. Infiltrating cytotoxic T cells, Treg, Th1 and Th17 cells of colorectal cancer patients were quantified by immunohistochemical analyses of tissue microarrays containing tissue cores from the center (CT) and from the invasive margin (IM) of the tumor. The inventors have surprisingly demonstrated that, contrary to patients with a high density of cytotoxic T cells, who have a prolonged disease-free survival, patients with a high density of Th17 cells (cells which express IL17, i.e. "IL17+ cells)) have, in general, a poor prognosis. In addition, when cell densities of both markers (Th17 and cytotoxic T cells) are taken into account, it becomes possible to discriminate amongst patients otherwise considered to simply have an "intermediate" survival prognoses based on cytotoxic T cell density alone. In particular, it has now been shown that patients with heterogeneous densities of cytotoxic T cells in the tumor center and invasive margin, who would otherwise be predicted to have an "intermediate" survival outcome, can be distinguished as having either good or bad survival prospects depending on the density of Th17 cells. The present invention thus provides methods for determining the prognosis of cancer patients based on Th17 cell densities; and for classifying as having either good or poor prognoses patients who were previously classified as having "intermediate" survival prospects based on cytotoxic T cell densities alone. This information advantageously enables health care professionals to better address the needs of cancer patients with increased specificity, and to adjust their treatment protocols accordingly.

The present invention thus relates to an in vitro method for predicting the survival time of a patient suffering from a solid cancer comprising the steps of i) providing (obtaining) a tissue tumor sample from the patient ii) determining in the tumor tissue sample the density of Th17 cells in the center and in the invasive margin of the tumor, iii) comparing the measured densities with predetermined reference values and iv) providing a good prognosis when both of the densities are lower than a predetermined reference value and a poor prognosis when both of the densities are higher than the predetermined reference value.

DETAILED DESCRIPTION OF THE INVENTION

The present invention relates to an in vitro method for predicting the survival time of a patient suffering from a solid cancer comprising the steps of i) providing (obtaining) a tissue tumor sample from the patient; ii) determining in the tumor tissue sample the density of Th17 cells in the centre and in the invasive margin of the tumor, iii) comparing said densities determined in step ii) with a predetermined reference value; and iv) providing a good prognosis when both of the densities are lower than the predetermined reference value and a poor prognosis when both of the densities are higher than the predetermined reference value. The method may further comprise the step of providing an intermediate prognosis if the densities are different (heterologous) i.e. one is higher than the corresponding reference value and the other is lower than the corresponding reference value.

In one embodiment the patient suffers from a cancer selected from the group consisting of adrenal cortical cancer, anal cancer, bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). Generally, the cancer is characterized by the presence of at least one solid tumor.

As used herein, the term "tumor tissue sample" has its general meaning in the art and encompasses pieces or slices of tissue that have been removed including following a surgical tumor resection or following the collection of a tissue sample for biopsy. The tissue tumor sample comprises the invasive margin and the centre of the tumor. As used herein the "invasive margin" has its general meaning in the art and refers to the cellular environment surrounding the tumor. The tumor tissue sample can, of course, be subjected to a variety of well-known post-collection preparative and storage techniques (e.g., fixation, storage, freezing, etc.) prior to determining the density of Th17 (and, optionally, cytotoxic T cells) at the invasive margin (IM) and center of the tumor. Typically the tissue tumor sample may be paraffin-embedded or frozen.

The method of the invention is particularly suitable for predicting (prognosing) the duration of the overall survival (OS) and/or the disease-free survival (DFS) of the cancer patient. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they've become cancer-free (achieved remission). DSF gives more specific information and is the number of people with a particular cancer who achieve remission. Also, progression-free (PF) survival rates (the number of people who still have cancer, but their disease does not progress) includes people who may have had some success with treatment, but the cancer has not disappeared completely.

As used herein, the term "Th17 cells" has its general meaning in the art and refers to a subset of T helper cells producing interleukin 17 (IL-17) (Steinman L (February 2007). "A brief history of T(H)17, the first major revision in the T(H)1/T(H)2 hypothesis of T cell-mediated tissue damage". Nat. Med. 13 (2): 139-145). The term "IL-1T" has its general meaning in the art and refers to the interleukin-17A protein. Typically, Th cells are characterized by classical expression of Th cell markers at their cell surface such as CD4, and by the expression of IL17. Typically, as referenced herein, a Th17 cell is a IL-17+ cell.

Determining the density of Th17 cells at the invasive margin of the tumor may be determined by any method known in the art. Typically, such methods comprise contacting the tumor tissue sample with at least one agent capable of selectively or specifically interacting with Th17 cells, e.g. by binding IL17. The selective agent may bind to Th17 cells, and may be a polyclonal antibody or a monoclonal antibody, an antibody fragment, a synthetic antibody, or another protein-specific agent such as a nucleic acid or peptide aptamer. Typically, the IL-17/Th17 cell selective or specific binding agent is an antibody. Several antibodies have been described in the prior art and many antibodies and are also commercially available (such as those described in the EXAMPLE 1). For the detection of the antibody that makes the presence of the Th17 cells detectable e.g. by microscopy or with an automated analysis system, the antibodies may be tagged and detected directly with one or more detectable labels (such as various enzymes, chromogens or fluorescent probes), or indirectly using e.g. a secondary antibody conjugated with detectable labels.

The preferred detection method according to the present invention is immunohistochemistry. Typically, the tissue tumor sample is first incubated with labelled antibodies directed against the Th17 marker IL-17. After washing, the labelled antibodies that are bound to the Th17 cell marker of interest are revealed by the appropriate technique, depending of the kind of label that is borne by the labelled antibody, e.g. a radioactive, fluorescent or enzyme label. Multiple labelling can be performed simultaneously. Alternatively, the method of the present invention may use a secondary antibody coupled to an amplification system (to intensify the staining signal) and enzymatic molecules. Such coupled secondary antibodies are commercially available, e.g. from Dako, EnVision system. Counterstaining may be used, e.g. hematoxylin and eosin (H&E), 4'-6-diamidino-2-phenylindole (DAFT), Hoechst, etc. Other staining methods may be accomplished using any suitable method or system as would be apparent to one of skill in the art, including automated, semi-automated or manual systems.

As used herein, the density of Th17 cells may be expressed as the number of these cells that are counted per one unit of surface area of tissue sample, e.g. as the number of Th17 cells that are counted per $cm^2$ or $mm^2$ of surface area of tumor tissue sample. As used herein, the density of Th17 cells may also be expressed as the number of Th17 cells per one volume unit of sample, e.g. as the number of Th17 cells per $cm^3$ of tumor tissue sample. As used herein, the density of Th17 cells may also consist of the percentage of Th17 cells per total cells (set at 100%).

Predetermined reference values used for comparison may comprise "cut-off" or "threshold" values that may be determined as described herein. Each reference ("cut-off") value for each biological marker may be predetermined by carrying out a method comprising the steps of a) providing or obtaining a collection or plurality of tumor tissue samples from a plurality of cancer patients;

b) providing, for each tumor tissue sample provided at step a), information relating to the actual clinical outcome for the corresponding cancer patient (i.e. the duration of the disease-free survival (DFS) and/or the overall survival (OS));

c) providing a scale comprising a series of arbitrary quantification values, which may be numbered, e.g. 1-n, where n is an integer greater than 1;

d) determining the Th17 cell density at the invasive margin and/or at the centre of the tumor for each tumor tissue sample contained in the collection provided at step a);

e) classifying the tumor tissue samples into two groups for a single (i.e. one) first selected specific arbitrary quantification value provided at step c), respectively, as follows: (i) a first group comprising tissue tumor samples that exhibit a quantification value for said density that is lower than the specific arbitrary quantification value that is selected from the series of arbitrary quantification values; (ii) a second group comprising tumor tissue samples each of which exhibit a quantification value for the density that is higher than the specific arbitrary quantification value selected from the series of quantification values; whereby two groups of tumor tissue samples are obtained for the selected specific quantification value, and wherein the tumor tissue samples of each group are separately enumerated and assigned a designation of higher or lower than the selected arbitrary quantification value;

f) calculating the statistical significance between (i) the quantification value obtained at step e) and (ii) the actual clinical outcome of the patients from which tumor tissue samples contained in the first and second groups defined at step f) derive;

g) reiterating steps f) and g) until every arbitrary quantification value provided at step d) is tested (i.e. performing steps f) and g) for a second, third, fourth etc. selected arbitrary quantification values up to and including the nth arbitrary quantification value of the set;

h) setting the predetermined reference value ("cut-off" value) as consisting of the specific arbitrary quantification value for which the highest statistical significance (most significant) is calculated at step g). In other words, the statistical significance for each of the 1-n arbitrary quantification values of the set are compared, and the arbitrary quantification value for which the statistical significance is highest is selected as the reference value.

As it is disclosed above, this method allows the setting of a single "cut-off" value that permits discrimination between a poor and a good prognosis with respect to DFS and OS. Practically, high statistical significance values (e.g. low P values) are generally obtained for a range of successive arbitrary quantification values, and not only for a single arbitrary quantification value. Thus, in one alternative embodiment of the method of determining "cut-off" values as above, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. According to this specific embodiment of a "cut-off" value, poor or good clinical outcome prognosis can be determined by comparing the Th17 cell density determined at step d) with the range of values which are identified. In certain embodiments, a cut-off value thus consists of a range of quantification values, e.g. centered on the quantification value for which the highest statistical significance value is found (e.g. generally the minimum P value which is found). For example, on a hypothetical scale of 1 to 10, if the ideal cut-off value (the value with the highest statistical significance) is 5, a suitable (exemplary) range may be from 4-6. Therefore, a patient may be assessed by comparing values obtained by measuring Th17 cell density in the center and IM of a tumor, where values greater than 5 indicate a poor prognosis and values less than 5 indicate a good prognosis; or a patient may be assessed by comparing values obtained by measuring Th17 cell density in the center and 1M of a tumor and comparing the values on a scale, where values above the range of 4-6 indicate a poor prognosis and values below the range of 4-6 indicate a good prognosis, with values falling within the range of 4-6 indicating an intermediate prognosis.

Typically, the predetermined reference values and the measured values are the measured density of Th17 cells within a defined area or volume of a tumor per the total number of cells (set at 100%) within the area or volume. The measured values may correlate with a poor prognosis (e.g. a short disease-free survival time), or in contrast may correlate with a good prognosis (e.g. a long disease-free survival time), depending on their value with respect to the predetermined reference values.

Figure 1A:
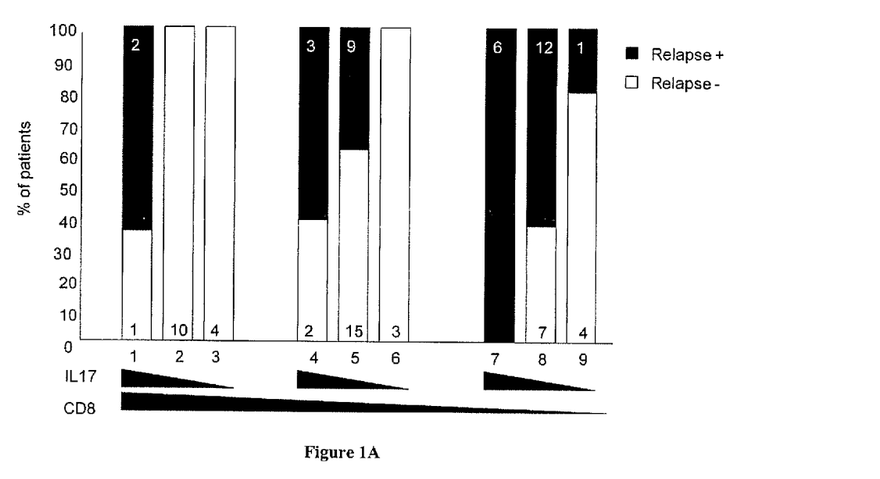
FIG. 1A-C: (A) The frequency of patients with (black columns) or without (white columns) relapse classified according to the densities of immune cells within colorectal tumors. Patients (n=71) were classified according to the CD8 and Th17 (IL17) cells densities in two regions of the tumor, the center and the invasive margin of the tumor. High CD8 densities in the two regions of CD8 were represented in histograms 1-3, heterogeneous densities in the histograms 4-6, and low densities in histograms 7-9. High densities in the two regions of IL17 were represented in the histograms 1, 4, 7, heterogeneous densities in the histograms 2, 5, 8, and low densities in the histograms 3, 6, 9. NA, not available. Kaplan Meier curves illustrate the duration of Disease free survival according to the IL17 cells density (B) in combination with CD8 cells density (C) in two regions of the tumor, the center and the invasive margin of the tumor. Groups of patients with low densities in the two regions were named LoLo, those with high densities in the two regions HiHi, and the others with heterogeneous densities Het. The cutoff value for the density of CD8 and IL17 cells were defined at the optimal p-value of the cohort. Hazard ratio (HR) and logrank p corrected values for DFS comparing patients with low against high gene expression.
Figure 1B:
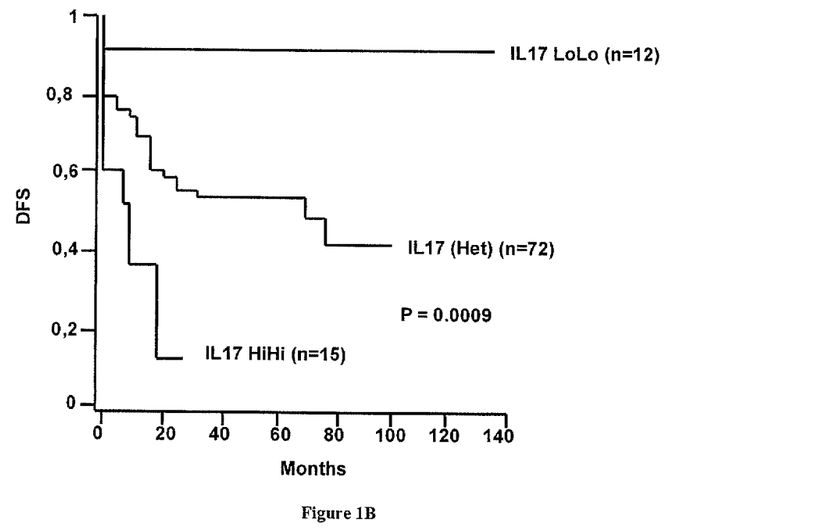

In a particular embodiment the method of the invention comprises comparison steps which include a classification of the quantification values measured for each cell density in two groups, as follows: (i) a first group termed "Hi" when the quantification value for cell density is higher than the predetermined corresponding reference value and (ii) a second group termed "Lo" when the quantification value for the cell density is lower than the predetermined corresponding reference value. It flows from the example that if the result of the comparison step consists of exclusively "Hi" values for Th17 cells, then a poor prognosis is provided (FIG. 1B and Table 1). Conversely, if the result of the comparison step consists of exclusively "Lo" values for Th17 cells, then a good prognosis is provided (FIG. 1B and Table 1). Intermediate conclusions are determined for "heterogeneous" or "het" patients, wherein, in the comparison step, "Hi" quantification values are found for one region (CT or IM) and "Lo" quantification values are found for the cell densities of the other region, as is disclosed in the examples herein. A score which is a composite of the classifications may also be calculated as depicted in Table 1 to make it easier to understand the results of the comparison step.

In a particular embodiment the method of the invention may further comprise the steps of i) determining the density of at least one additional T cell subset at the invasive margin and at the centre of the tumor (CT) in a tumor tissue sample obtained from said patient and ii) comparing said densities with predetermined reference values. Typically the additional cell subset is cytotoxic T cells (e.g. CD8 cells), although other T cell subsets may also be used. For example, CD3 or granzyme B (GMBZ) cells, or other T cells that are known in the art. The values obtained for the at least one other T cell subset type may be used to confirm or refine the prognosis that is arrived at by analyzing only Th17 cells, e.g. by providing a composite score that includes results for the at least one other T cell subset. This option is illustrated in Table 3.

As used herein the term "cytotoxic T cells" has its general meaning in the art and refers to a T cell that, once activated by a MHC-antigen complex, releases the protein perforin, which forms pores in the target cell's plasma membrane; this causes ions and water to flow into the target cell, making it expand and eventually lyse. Cytotoxic T cells also release granzyme, a serine protease that can enter target cells via the perform-formed pore and induce apoptosis (cell death). Most cytotoxic T cells have the protein CD 8 present on their cell surfaces. CD8 is attracted to portions of the Class I MHC molecule. Typically, a cytotoxic T cell is a CD8+ cell. In one embodiment, the method of the invention may further comprise the steps of i) determining the density of cytotoxic T cells at the invasive margin (IM) and in the center of the tumor (CT); and ii) comparing the cytotoxic T cell densities with predetermined reference values.

For the additional T cell subset, the comparison steps may also include a classification of the quantification values measured for each cell density in two groups, respectively: (i) a first group termed "Hi" when the quantification value for cell density is higher than a predetermined corresponding reference value and (ii) a second group termed "Lo" when the quantification value for the cell density is lower than the predetermined corresponding reference value. Methods of assessing CD8 cells are described, for example, in pending U.S. application Ser. No. 12/090,832, the complete contents of which are hereby incorporated by reference in entirety.

Finally, a final score that is a composite of the Th17 cell densities and the cytotoxic T cell densities may be calculated as illustrated in Tables 2-4.

The methods of the invention are of higher accuracy than currently used staging methods (e.g. UICC-TNM). Accordingly, the methods of the invention can be applied for monitoring the effectiveness of anti-cancer treatments. For example, the present invention provides a method for monitoring the effectiveness of treatment of a subject with an anti-cancer agent comprising the steps of (i) predicting the survival time of the patient before administering the anti-cancer agent by performing the method of the invention; ii) predicting the survival time of the patient after administering the anti-cancer agent by performing the method of the invention; iii) comparing the survival time of step i) with the survival time of step ii) and iv) and concluding that the agent is effective for the treatment of the cancer when the survival time of step ii) is higher than the survival time of step i). In cases where the conclusion is negative (e.g. when the survival time of step ii) is the same or lower than the survival time of step i)), then the physician may change or adapt the treatment by prescribing different dosages of the anti-cancer agent, by prescribing another agent to administer, etc. Conversely, when a positive conclusion is reached, treatment may be continued without changes. Monitoring of treatment efficacy may be continued in this manner over the entire period of treatment, and/or to inform or determine the length of the treatment (e.g. treatment may be continued so long as improvement is observed), or to discontinue treatment at any point at which improvement is no longer observed.

The methods of the invention may also be particularly suitable for determining whether a patient will be considered as a responder to (and hence a good candidate for) a treatment using e.g. an immunotherapy agent. Typically, when a good prognosis is provided by the methods of the invention, the patient may be considered likely to benefit from and thus eligible for the treatment. The methods of the invention may also particularly suitable for determining whether adjuvant therapy (e.g. chemotherapy) will be required or not. For example, when a good prognosis is provided by the method of the invention, the subsequent anti-cancer treatment may not be deemed to require any adjuvant chemotherapy. However, when a poor prognosis is provided by the method of the invention, then the patient may be better treated using an aggressive regime such as adjuvant chemotherapy.

The present invention includes a kit for performing the method of the present invention comprising means for determining cell densities as above described. For example, a kit according to the invention may comprise one or a combination or set of antibodies, each antibody being directed specifically or selectively against one cell type such as Th17 cells and, optionally, cytotoxic T cells. Suitable means include antibodies, antibody derivatives, antibody fragments, and the like. The kit of the invention may optionally comprise additional components useful for performing the methods of the invention. By way of example, the kit may comprise fluids (e.g. buffers), one or more sample compartments, instructional material which describes performance of the method of the invention, including a list of predetermined reference values, and the like. In addition, a kit may include this and additional information either as printed material, or on a suitable storage medium, e.g. a CD, DVD or other medium on which such information can be recorded. In addition, the medium may contain instructions for programming a computer to carry out the steps of the method, e.g. for receiving as input cell density values measured using the method, and calculating a patient's prognosis based on those values. The result may be provided, for example, on a display such as a computer screen or as a hard copy, or in some other manner.

The invention will be further illustrated by the figures and by the following examples. However, the examples and figures should not be interpreted in any way as limiting the scope of the present invention.

EXAMPLE 1

Material & Methods
Patients and Database
Patients with colorectal cancer who underwent a primary resection at the Laennec/HEGP (Hopital Europpéen George Pompidou) Hospital between 1986 and 2004 were randomly selected (cohort 1, n=125 and cohort 2, n=106). The validation cohort (n=415) was previously described (Galon J, Costes A, Sanchez-Cabo F, et al. Type, density, and location of immune cells within human colorectal tumors predict clinical outcome. Science 2006; 313:1960-4). Time to recurrence or disease-free time was defined as the time period from the date of surgery to the confirmed tumor relapse date for relapsed patients and from the date of surgery to the date of last follow-up for disease-free patients. A secure Web-based database, TME.db, integrated the clinical data and the data from high-throughput technologies (Mlecnik B, Sanchez-Cabo F, Charoentong P, et al. Data integration and exploration for the identification of molecular mechanisms in tumor-immune cells interaction. BMC Genomics 2010; 11 Suppl 1:S7).

Tissue Microarrays Construction

Using a tissue microarray instrument (Beecher Instruments, Alphelys, Plaisir, France), we selected two different and representative areas of the tumor. The center of the tumor (CT) and the invasive margin (IM) were punched (0.6 mm and 1 mm-diameter, respectively) from paraffin-embedded tissue-blocks. Tissue microarrays were constructed and cut into 5-μm sections for immunohistochemical staining.

Immunohistochemistry

After antigen retrieval and quenching of endogenous peroxidase activity, sections were incubated for 60 min at room temperature with antibodies against CD8 (4B11; Neomarkers, Fremont, Calif.), FoxP3 (ab20034; abeam, Cambridge, United Kingdom), CCL5 (NBP1-19769), RORC (NLS5188; Novus Biological, Littleton, USA), T-bet (4B10), CCL24 (G-17) and IL17 (H-132; Santa Cruz Biotechnology, Santa Cruz, Calif.). Envision+ system (enzyme-conjugated polymer backbone coupled to secondary antibodies) and DAB-chromogen were applied (Dako, Copenhagen, Denmark). Tissue sections were counter-stained with Harris's hematoxylin. Slides were analyzed using an image analysis workstation (SpotBrowser, Alphelys, Plaisir, France). The density was recorded as the number of positive cells per tissue surface area ($mm^2$). For each duplicate, the mean density was used for further statistical analysis.

Statistical Analysis

Genesis software was used to visualize and cluster the correlation matrix and gene expression. Kaplan-Meier curves were used to assess the influence of immune parameters on disease-free survival. The significance of these parameters was calculated with the log-rank test. We applied two different methods to assess the cutoffs for the separation of patients, and similar results were found. First, we used hierarchical clusters of gene expression data (LDA) to define the cutoffs. Second, we applied cutoffs based on the patients' disease-free survival using the median and "minimum P-value" approach to separate patients into a Hi and Lo group. For pairwise comparisons Wilcoxon rank-sum test was used. P<0.05 was considered statistically significant. All analyzes were performed with the statistical software R and Statview.

Results

In situ studies using tissue microarray from the center and the invasive margin of the tumor were performed. Immunostaining for Th1 (CD8, T-bet), Th17 (IL17) and regulatory T cells (FOXP3) were quantified with a dedicated image analysis workstation. A precise measurement of intratumoral immune cell density was performed by counting the immune cells and measuring the surface area of the tissue.

Figure 1C:
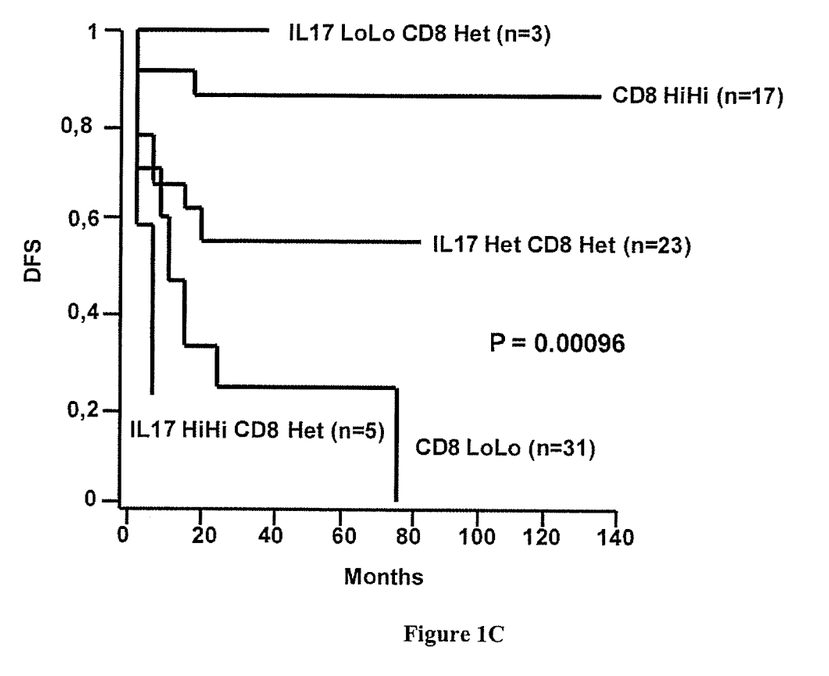
Figure 2:
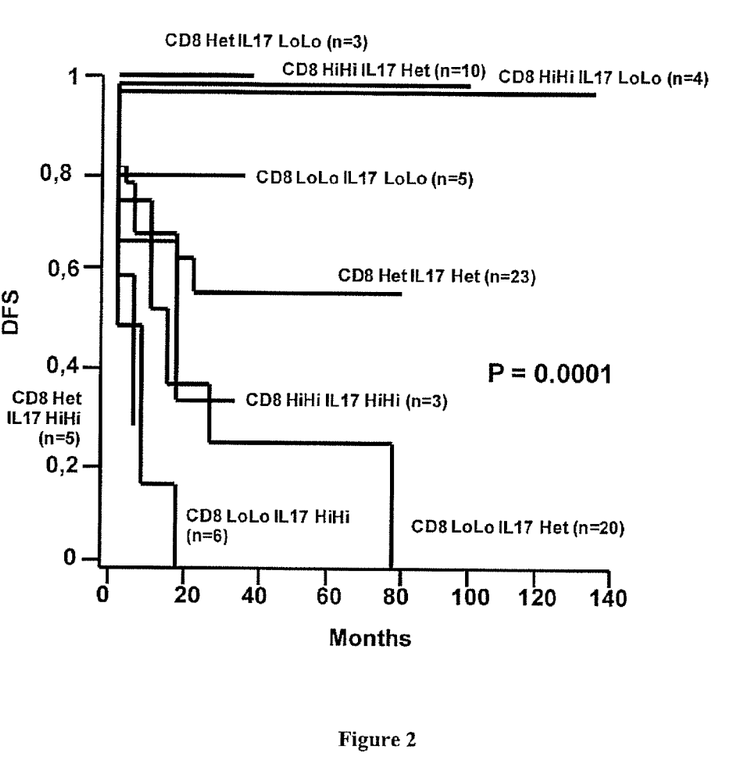
FIG. 2: Kaplan Meier curves illustrate the duration of disease free survival according to IL17 cell density in combination with CD8 cell density in two regions of the tumor, the center and the invasive margin. The cutoff value for the density of IL17 and CD8 cells was defined at the optimal p-value of the cohort.
Figure 3A:
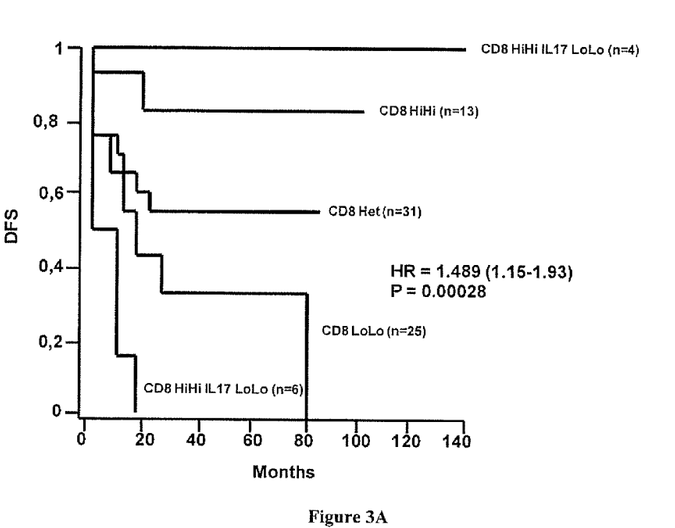
FIG. 3A-B: Kaplan Meier curves illustrate the duration of disease free survival according to IL17 cell density in combination with CD8 cell density in two regions of the tumor, the center and the invasive margin. Panel (A) illustrates cohort 2 (n=106 patients), and panel (B) illustrates the validation cohort (n=415).
Figure 3B:
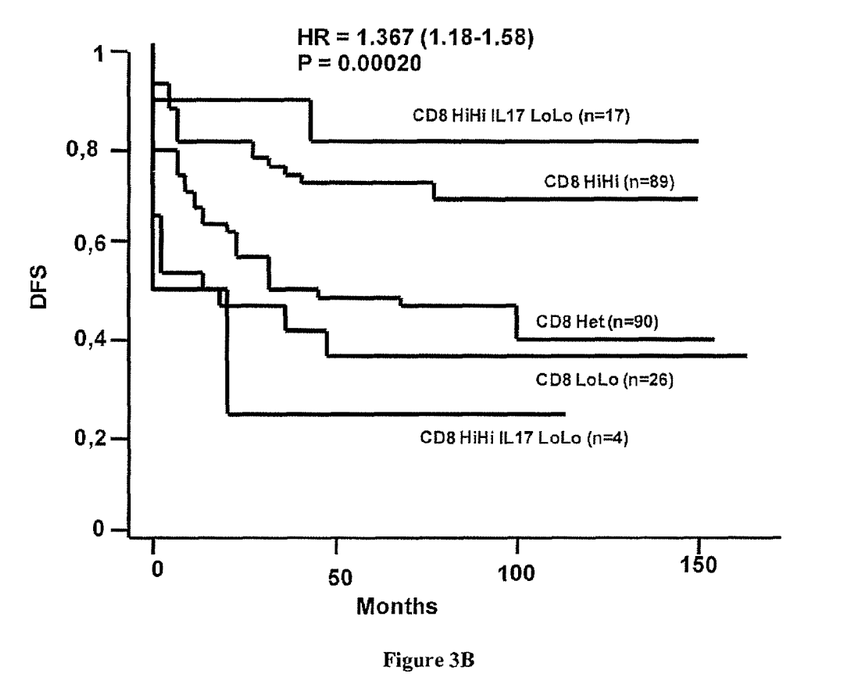

The percentage of the relapsing patients decreased with the CD8 density (FIG. 1A): 11.7%, 37.5% and 63.3% inCD8 HiHi, Het, LoLo patients groups, respectively. Contrary to CD8, the frequency of relapsing patients increased with the IL17 density (63.3%, 0%, 0% in IL17 HiHi, Het, LoLo and CD8 HiHi patient groups, 60%, 37.5%, 0% in IL17 HiHi, Het, LoLo and CD8 Het patient groups and 100%, 63.2%, 20% in IL17 HiHi, Het, LoLo and CD8 LoLo patients groups respectively). We evaluated the disease-free survival according to the Th1 and Th17 cell density. Kaplan-Meier curves illustrated the pejorative effect of IL17A on patient's survival. Patients with low IL17 density in the two regions of the tumors had a better disease-free survival than patients with high IL17 density in both regions (FIG. 1B, HR=3.08, p=0.0009). Indeed, 70% of the patients in the LoLo group did not relapse. In contrast, 50% of the patients in the HiHi group had tumor recurrence after one year. The combination of the CD8 and IL17 markers defined groups of patients with very different outcomes. Patients with CD8 LoLo had a dramatic outcome. Median disease-free survival was 9 months and all patients experienced tumor recurrence after 6 years. In contrast, patients with CD8 HiHi had a very good outcome and patients with CD8-HiHi and a low density of IL17+ cells (IL17-LoLo) had the best outcome (FIG. 2, HR=1.48, p=0.0009). Strikingly, in the group of patients with heterogeneous density of CD8, patients with low density of IL17 had a better disease-free survival whereas patients with high density of IL17 had a poor prognosis (FIG. 1C and FIG. 2). 8% of patients relapsed in the group of patients with low density of IL17 cells whereas 40% and 70% of patients in the IL17-Het and IL17-HiHi groups relapsed, respectively. The longest disease-free survival was observed among patients with tumors containing a high density of CD8+ cells and a low density of IL17+ cells (Table 3). We validated the results by analyzing an independent cohort of 415 colorectal cancer patients by tissue microarrays. Similar results were found (FIGS. 3A and 3B). Longer disease-free survival was observed among patients with tumor containing a high density of CD8+ cells (CD8-HiHi), and patients with CD8-HiHi and a low density of IL17+ cells (IL17-LoLo) had the best outcome (FIGS. 3A and 3B). Patients with CD8-LoLo had a very bad outcome. Strikingly, the group of patients with CD8-LoLo and with high density of IL17 (IL17-HiHi) had the worst prognosis. Similar hazard-ratios and P-values were found in both cohorts (HR=1.49 and HR=1.37, P=0.0002, respectively).

Finally, we performed multivariate analyses integrating the classical clinical parameters with the immune score. We applied stepwise Akaike information criterion (AIC)-based Cox multivariate analysis to reduce the number of parameters to the most informative ones. Table 4 shows that the immune parameter (CD8/IL17) in the whole as well as in the reduced model remains significant.

CONCLUSION

In conclusion, patients with high density of IL17+ cells had a poor prognosis whereas patients with high density of CD8+ cells had a prolonged disease-free survival. The combination of these two markers gave also a better discrimination of patients. In particular, patients with heterogeneous densities of CD8 cells between tumor regions having an intermediate outcome could be discriminated as having good or bad survival prospects, depending on the densities of the IL17+ cells.

TABLE 1

IL17 combinations

| Name | Combination | Prognosis | Score |
|---|---|---|---|
| Th17 LoLo | IL-17 "Lo" (Ct)/IL-17 "Lo" (Im) | Good | 2 |
| Th17 Het | IL-17 "Lo" (Ct)/IL-17 "Hi" (Im) or IL-17 "Hi" (Ct)/IL-17 "Lo" (Im) | Intermediate | 1 |
| Th17 HiHi | IL-17 "Hi" (Ct)/IL-17 "Hi" (Im) | Poor | 0 |

TABLE 2

CD8/IL-17 combinations:

| Combination | Prognosis | Score |
|---|---|---|
| CD8 HiHi/IL-17 LoLo | Good | 4 |
| CD8 HiHi/Il-17 Het | Good | 3 |
| CD8 Het/IL-17 LoLo | Good | 3 |
| CD8 LoLo/IL-17 LoLo | Intermediate | 2 |
| CD8 HiHi/IL-17 HiHi | Intermediate | 2 |
| CD8Het/IL-17 HiHi | Poor | 1 |
| CD8 LoLo/IL-17 Het | Poor | 1 |
| CD8 LoLo/IL-17 HiHi | Poor | 0 |

TABLE 3

Multivariate analysis of Disease-free survival (DFS) among patients with AJCC/UICC-TNM Stage I/II/III/IV colorectal cancer cohort 2 (TMA 106 pts) according to clinical parameters or immune parameters

| | No. of patients (percentage) | Rate at 5 yr % (95% CI) | Hazard ratio (95% CI) | P value* | P value* ** | Hazard ratio (95% CI) | P value* | P value** |
|---|---|---|---|---|---|---|---|---|
| CD8 CT | | | | | | 0.26 (0.13-0.54) | 0.0001 s | 0.0047 s |
| Lo | 55 (53.4) | 32.4 (19.9-52.6) | 3.78 (1.86-7.66) | 0.0001 | 0.0047 s | | | |
| Hi | 48 (46.6) | 76.2 (63.9-90.9) | 1.0 (reference) | | | | | |
| CD8 IM | | | | | | 0.37 (0.16-0.84) | 0.0138 s | 0.3955 |
| Lo | 56 (65.9) | 42 (29.5-59.9) | 2.73 (1.19-6.27) | 0.0138 | 0.3955 | | | |
| Hi | 29 (34.1) | 68.5 (51-92) | 1.0 (reference) | | | | | |
| CD8 CT/IM | | | | | | 0.39 (0.23-0.65) | 0.0005 s | 0.0276 s |
| LoLo | 33 (39.3) | 24.4 (11-54.4) | 11.08 (2.54-48.43) | 0.0001 | 0.0053 s | | | |
| Het | 32 (38.1) | 55.9 (39-79.9) | 4.5 (1-20.19) | 0.0306 | 0.6726 | | | |
| HiHi | 19 (22.6) | 87.4 (72.4-100) | 1.0 (reference) | | | | | |
| IL17 CT | | | | | | 7.11 (0.98-51.66) | 0.0206 s | 0.5200 |
| Lo | 14 (13.5) | 92.9 (80.3-100) | 0.14 (0.02-1.02) | 0.0206 | 0.5200 | | | |
| Hi | 90 (86.5) | 48.4 (38.1-61.5) | 1.0 (reference) | | | | | |
| IL17 IM | | | | | | 2.78 (1.38-5.6) | 0.0031 s | 0.1277 |
| Lo | 85 (84.2) | 58 (47.1-71.5) | 0.36 (0.18-0.72) | 0.0031 | 0.1277 | | | |
| Hi | 16 (15.8) | 20.8 (6.6-65.7) | 1.0 (reference) | | | | | |
| IL17 CT/IM | | | | | | 3.08 (1.67-5.7) | 0.0009 s | 0.0475 s |
| LoLo | 12 (12.1) | 91.7 (77.3-100) | 0.08 (0.01-0.64) | 0.0021 | 0.0935 | | | |
| Het | 72 (72.7) | 54.4 (42.9-68.9) | 0.35 (0.17-0.71) | 0.0024 | 0.1041 | | | |
| HiHi | 15 (15.2) | 12.5 (2.2-71.1) | 1.0 (reference) | | | | | |
| Immune Score CD8/IL17 | | | | | | 0.68 (0.53-0.87) | 0.0010 s | 0.0494 s |
| I0 | 31 (39.2) | 25.1 (11.3-55.8) | 10.07 (2.29-44.22) | 0.0002 | 0.0119 s | | | |
| I1-IL17 LoLo | 3 (3.8) | 100 (100-100) | NaN (NaN-NaN) | NaN | NaN | | | |
| I1-IL17 Het | 23 (29.1) | 56.7 (38.2-83.9) | 3.91 (0.84-18.16) | 0.0590 | NaN | | | |
| I1-IL17 HiHi | 5 (6.3) | 30 (6.3-100) | NaN (NaN-NaN) | NaN | NaN | | | |

TABLE 3-continued

Multivariate analysis of Disease-free survival (DFS) among patients with
AJCC/UICC-TNM Stage I/II/III/IV colorectal cancer cohort 2 (TMA 106 pts) according
to clinical parameters or immune parameters

|  | No. of patients (percentage) | Rate at 5 yr % (95% CI) | Hazard ratio (95% CI) | P value* | P value* ** | Hazard ratio (95% CI) | P value* | P value** |
|---|---|---|---|---|---|---|---|---|
| I2 | 17 (21.5) | 86.3 (70.1-100) | 1.0 (reference) | | | | | |

† The stage was determined by pathological (p) examination. Tis denotes carcinoma in situ, T1 tumor invading submucosa, T2 tumor invading muscularis propria, T3 tumor penetrating muscularis propria and invading subserosa, and T4 tumor completely through the intestine's wall and invading serosa and nearby tissues.
: Bowel perforation presentation.
*Log-rank P value.
**P value correction with Altman et al.
Het: Hi/Lo and Lo/Hi.
NR: Not Reached.
s: significant.
CI denotes confidence interval.
CT: center of the tumor and
IM: Invasive margin.
I0: CD8 LoLo,
I1: CD8 Het and
I2: CD8 HiHi.

TABLE 4

Multivariate proportional hazard Cox analysis for DFS among patients with UICC-TNM
Stage I/II/III/IV colorectal cancer Clinical parameters + Immune Score CD8/IL17

| Variable | PHA test *** | Hazard ration | (95% CI) | P-value |
|---|---|---|---|---|
| Age (yrs) (<65 = 0, 65-75 = 1, 75-85 = 2, >85 = 3) | 0.9538 | 1.01 | (0.67-1.53) | 0.9551 |
| Tumor (T) stage (TisT1 = 0, T2 = 1, T3 = 2, T4 = 3) | 0.8819 | 2.64 | (1.24-5.61) | 0.0118 |
| N stage (N0 = 0, N1 = 1, N2 = 2) | 0.0035 | s1.20 | (0.76-1.89) | 0.4365 |
| Tumor Location (Left colon = 0, Right colon = 1, Transverse colon = 2, Sigmoid colon = 3, Rectum = 4) | 0.3126 | 0.89 | (0.67-1.18) | 0.4082 |
| Histological grade (Well differentiated = 0, Moderately differentiated = 1, Poor differentiated = 2) | 0.4494 | 0.97 | (0.48-1.96) | 0.9280 |
| Mucinous Colloide Type (No = 0, Yes = 1) | 0.4801 | 1.08 | (0.42-2.75) | 0.8767 |
| Occlusion (No = 0, Yes = 1) | 0.2639 | 0.81 | (0.23-2.9) | 0.7454 |
| Perforation (No = 0, Yes = 1) | 0.8252 | 0.79 | (0.09-7.35) | 0.8370 |
| Immune Score CD8/IL17 (I0 = 0, I1-IL17LoLo = 1, I1-IL17Het = 2, I1-IL17HiHi = 3, I2 = 4) | 0.0347 | s0.66 0.69** | (0.49-0.89) (0.52 | 0.0073 |
| Final Model for DFS after stepwise (stepAIC) selection | | | | |
| Tumor (T) stage (TisT1 = 0, T2 = 1, T3 = 2, T4 = 3) | 0.5720 | 2.64 | (1.35-5.16) | 0.0045 |
| Immune Score CD8/IL17 (I0 = 0, I1-IL17LoLo = 1, I1-IL17Het = 2, I1-IL17HiHi = 3, I2 = 4) | 0.0510 | 0.67 0.68** | (0.51-0.88) | 0.0034 |

**Leave-one-out method, correction using C = 1-

* Immune Score: CD8CT/IMCD45ROCT/IM, minimum P -value cut-off with 4 groups: (Im4)-4Hi. (Im3)-3Hi, (Im2)-2Hi, (Im1)-1Hi), (Im0)-0Hi)
**heuristic shrinkage factor. Corrected by Hollaender et al. Similar results obtained using bootstrap. #: Bowel perforation presentation (Yes, No).
*** PHA (proportional hazards assumption) test (P < 0.05 violates the hazards assumption)

REFERENCES

1. Dunn G P, Old L J, Schreiber R D. The three Es of cancer immunoediting. Annu Rev Immunol 2004; 22:329-60.

2. Balkwill F, Coussens L M. Cancer: an inflammatory link. Nature 2004; 431:405-6.

3. Coussens L M, Werb Z. Inflammation and cancer. Nature 2002; 420:860-7.

4. Galon J, Costes A, Sanchez-Cabo F, et al. Type, density, and location of immune cells within human colorectal tumors predict clinical outcome. Science 2006; 313:1960-4.

5. Marrogi A J, Munshi A, Merogi A J, et al. Study of tumor infiltrating lymphocytes and transforming growth factor-beta as prognostic factors in breast carcinoma. Int J Cancer 1997; 74:492-501.

6. Menegaz R A, Michelin M A, Etchebehere R M, Fernandes P C, Murta E F. Peri- and intratumoral T and B lymphocytic infiltration in breast cancer. Eur J Gynaecol Oncol 2008; 29:321-6.

7. Al-Shibli K I, Donnem T, Al-Saad S, Persson M, Bremnes R M, Busund L T. Prognostic effect of epithelial and stromal lymphocyte infiltration in non-small cell lung cancer. Clin Cancer Res 2008; 14:5220-7.

8. Dieu-Nosjean M C, Antoine M, Danel C, et al. Long-term survival for patients with non-small-cell lung cancer with intratumoral lymphoid structures. J Clin Oncol 2008; 26:4410-7.

9. Hiraoka K, Miyamoto M, Cho Y, et al. Concurrent infiltration by CD8+ T cells and CD4+ T cells is a favourable prognostic factor for non-small-cell lung carcinoma. Br J Cancer 2006; 94:275-80.

10. Ito N, Suzuki Y, Taniguchi Y, Ishiguro K, Nakamura H, Ohgi S. Prognostic significance of T helper 1 and 2 and T cytotoxic I and 2 cells in patients with non-small cell lung cancer. Anticancer Res 2005; 25:2027-31.

11. Kawai 0, Ishii G, Kubota K, et al. Predominant infiltration of macrophages and CD8(+) T Cells in cancer nests is a significant predictor of survival in stage IV nonsmall cell lung cancer. Cancer 2008; 113:1387-95.

12. Pages F, Berger A, Camus M, et al. Effector memory T cells, early metastasis, and survival in colorectal cancer. N Engl J Med 2005; 353:2654-66.

13. Camus M, Tosolini M, Mlecnik B, et al. Coordination of intratumoral immune reaction and human colorectal cancer recurrence. Cancer Res 2009; 69:2685-93.

Throughout this application, various references describe the state of the art to which this invention pertains. The disclosures of these references are hereby incorporated by reference into the present disclosure.

The invention claimed is:
1. An in vitro method for the prognosis of survival time and treatment of a patient suffering from a solid cancer, comprising the steps of:
  a) measuring i) a center (CT) density of IL17+cells in a prepared tumor tissue sample from the center of a tumor from said patient and ii) an invasive margin (IM) density of IL17+cells in a tumor tissue sample from the invasive margin of said tumor;
    wherein said step of measuring is performed by
      contacting the prepared tumor tissue sample with at least one agent that specifically or selectively binds to IL17 and is labeled directly with a detectable label or indirectly with a detectable label, and
      detecting binding of the at least one agent to the prepared tumor tissue sample;
  b) comparing i) said CT density to a predetermined CT density reference value and ii) said IM density to a predetermined IM density reference value; and
  c) providing a favorable prognosis of survival time for said patient when said CT density is lower than said predetermined CT density reference value and said IM density is lower than said predetermined IM density reference value; or
    providing an unfavorable prognosis of survival time for said patient when said CT density is higher than said predetermined CT density reference value and said IM density is higher than said predetermined IM density reference value; or
    providing an intermediate prognosis of survival time for said patient when one of said CT density and said IM density is higher and the other of said CT density and said IM density is lower than a corresponding density reference value; and
  d) treating the patient with an anticancer treatment selected based on c).

2. The in vitro method according to claim 1, wherein step a) is performed by immunodetection.

3. The method of claim 2 wherein the anti-IL-17 antibody comprises a detectable label.

4. The in vitro method according to claim 1, wherein the cancer is colorectal cancer.

5. The method of claim 4 wherein the anti-IL-17 antibody is detected indirectly using a secondary antibody.

6. The in vitro method according to claim 1, further comprising the steps of: i) measuring a CT density and an IM density of at least one additional type of cell; ii) comparing said CT density and said IM density of at least one additional type of cell to corresponding predetermined CT density reference values and iii) using results obtained in said step of comparing to confirm or further refine said favorable prognosis, said unfavorable prognosis or said intermediate prognosis.

7. The method of claim 6, wherein said at least one additional type of cell is selected from the group consisting of cytotoxic T cells, CD3 cells, GZMB cells and regulatory T cells.

8. The method of claim 7, wherein said at least one additional type of cell is cytotoxic T cells.

9. The method according to claim 1, wherein said measuring step is performed by using at least one agent for detecting IL17+cells in a tumor sample and at least one agent for detecting at least one additional type of cell.

10. The method according to claim 9, wherein said at least one agent for detecting at least one additional type of cell is an agent for detecting cytotoxic T cells.

11. The method according to claim 10, wherein said at least one agent for detecting IL17+cells and said at least one agent for detecting at least one additional type of cell are antibodies.

12. The method of claim 1 wherein IL17+cell density is measured by contacting the tumor tissue sample with an anti-IL-17 antibody.

13. The in vitro method according to claim 1, wherein said solid cancer is selected from the group consisting of adrenal cortical cancer, anal cancer, bile duct cancer bladder cancer, brain and central nervous system cancer, breast cancer, cervical cancer, colorectal cancer, endometrial cancer, esophagus cancer, gallbladder cancer, gastrointestinal carcinoid tumors, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer.

14. The method of claim 1, wherein said prepared tissue sample is obtained by
  obtaining, following resection or biopsy of the solid cancer, a tumor tissue sample, and
  subjecting the tumor tissue sample to a preparative and/or storage technique.

15. The method of claim 1, wherein the at least one agent that specifically or selectively binds to IL17 is selected from the group consisting of a polyclonal antibody, a monoclonal antibody, an antibody fragment, a synthetic antibody, a nucleic acid aptamer, and a peptide aptamer.

16. The method of claim 1, wherein the at least one agent that specifically or selectively binds to IL17 is labeled directly with radioactivity, fluorescence, or enzyme labeling.

17. The method of claim 1, wherein the at least one agent that specifically or selectively binds to IL17 is labeled directly with a secondary antibody.

18. An in vitro method for the prognosis of disease-free survival (DFS) time and treatment of a patient suffering from a solid cancer, comprising the steps of:
  a) measuring i) a center (CT) density of IL17+cells in a prepared tumor tissue sample from the center of a tumor from said patient and ii) an invasive margin (IM) density of IL17+cells in a tumor tissue sample from the invasive margin of said tumor;
    wherein said step of measuring is performed by
      contacting the prepared tumor tissue sample with at least one agent that specifically or selectively binds to IL17 and is labeled directly with a detectable label or indirectly with a detectable label, and detecting binding of the at least one agent to the prepared tumor tissue sample;

b) comparing i) said CT density to a predetermined CT density reference value and ii) said IM density to a predetermined IM density reference value; and c) providing a favorable prognosis of DFS time for said patient when said CT density is lower than said predetermined CT density reference value and said IM density is lower than said predetermined IM density reference value; or providing an unfavorable prognosis of DFS time for said patient when said CT density is higher than said predetermined CT density reference value and said IM density is higher than said predetermined IM density reference value; or providing an intermediate prognosis of DFS time for said patient when one of said CT density and said IM density is higher and the other of said CT density and said IM density is lower than a corresponding density reference value; and d) treating the patient with an anticancer treatment selected based on c).

19. An in vitro method for the prognosis of overall survival (OS) time and treatment of a patient suffering from a solid cancer, comprising the steps of:

a) measuring i) a center (CT) density of IL17+cells in a prepared tumor tissue sample from the center of a tumor from said patient and ii) an invasive margin (IM) density of IL17+cells in a tumor tissue sample from the invasive margin of said tumor;

wherein said step of measuring is performed by contacting the prepared tumor tissue sample with at least one agent that specifically or selectively binds to IL17 and is labeled directly with a detectable label or indirectly with a detectable label, and detecting binding of the at least one agent to the prepared tumor tissue sample;

b) comparing i) said CT density to a predetermined CT density reference value and ii) said IM density to a predetermined IM density reference value; and c) providing a favorable prognosis of OS time for said patient when said CT density is lower than said predetermined CT density reference value and said IM density is lower than said predetermined IM density reference value; or providing an unfavorable prognosis of OS time for said patient when said CT density is higher than said predetermined CT density reference value and said IM density is higher than said predetermined IM density reference value; or providing an intermediate prognosis of OS time for said patient when one of said CT density and said IM density is higher and the other of said CT density and said IM density is lower than a corresponding density reference value; and d) treating the patient with an anticancer treatment selected based on c).

20. A method of treating a patient suffering from a solid cancer comprising, prognosing a survival time of said patient by:

a) measuring i) a center (CT) density of IL17+cells in a tumor tissue sample from the center of a tumor from said patient and ii) an invasive margin (IM) density of IL17+cells in a tumor tissue sample from the invasive margin of said tumor;

b) comparing i) said CT density to a predetermined CT density reference value and ii) said IM density to a predetermined IM density reference value; and c) providing a favorable prognosis of survival time for said patient when said CT density is lower than said predetermined CT density reference value and said IM density is lower than said predetermined IM density reference value; or providing an unfavorable prognosis of survival time for said patient when said CT density is higher than said predetermined CT density reference value and said IM density is higher than said predetermined IM density reference value; or providing an intermediate prognosis of survival time for said patient when one of said CT density and said IM density is higher and the other of said CT density and said IM density is lower than a corresponding density reference value, and if an unfavorable prognosis of survival time for said patient is provided treating the patient with aggressive adjunct therapy, and if a favorable prognosis of survival time for said patient is provided, treating the patient with immunotherapy.

21. The method of claim 20, wherein the solid cancer is a colorectal cancer or a non-small cell lung cancer.

22. A method of refining in vitro an intermediate prognosis of survival time of and treating a patient suffering from a solid cancer comprising:

identifying a patient with an intermediate prognosis of survival time, wherein said intermediate prognosis is determined by measuring both the center (CT) density of CD8 cells and the invasive margin (IM) density of CD8 cells in a prepared tumor tissue sample from the patient, by contacting the prepared tumor tissue sample with at least one agent that specifically or selectively binds to CD8 and is labeled directly with a detectable label or indirectly with a detectable label, and detecting binding of the at least one agent to the prepared tumor tissue sample; and comparing the CD8 CT density with a predetermined CD8 CT density reference value, wherein the patient is identified as having an intermediate prognosis of survival time when only one of the CD8 CT density and the CD8 IM density is higher than the corresponding predetermined CD8 CT density reference value and predetermined CD8 IM reference value; and refining the intermediate prognosis of survival time for said patient by measuring both a CT density IL17+cells and an IM density IL17+cells in a tumor tissue sample from the patient, comparing the IL17+CT density with a predetermined IL17+CT density reference value, and comparing the IL17+IM density with a predetermined IL17+IM density reference value, wherein the patient is identified as having a favorable prognosis of survival time when both of the IL17+CT density and the IL17+IM density are lower than the corresponding predetermined IL17+CT density reference value and predetermined IL17+IM reference value, and wherein the patient is identified as having a unfavorable prognosis of survival time when both of the IL17+CT density and the IL17+IM density are higher than the corresponding predetermined IL17+CT density reference value and predetermined IL17+IM reference value; and treating the patient with an anticancer treatment selected based on the refining step.

23. The method of claim 22, wherein IL17+cell density is measured by contacting the tumor tissue sample with an anti-IL-17 antibody.

24. The method of claim 22, wherein the anti-IL-17 antibody comprises a detectable label.

25. The method of claim 22, wherein the anti-IL-17 antibody is detected indirectly using a secondary antibody.

26. The in vitro method of claim 22, wherein the solid cancer is a colorectal cancer or a non-small cell lung cancer.

27. The method of claim 22, wherein said prepared tissue sample is obtained by
- obtaining, following resection or biopsy of the solid cancer, a tumor tissue sample, and
- subjecting the tumor tissue sample to a preparative and/or storage technique.

28. The method of claim 22, wherein the at least one agent that specifically or selectively binds to IL17 is selected from the group consisting of a polyclonal antibody, a monoclonal antibody, an antibody fragment, a synthetic antibody, a nucleic acid aptamer, and a peptide aptamer.

29. The method of claim 22, wherein the at least one agent that specifically or selectively binds to IL17 is labeled directly with radioactivity, fluorescence, or enzyme labeling.

30. The method of claim 22, wherein the at least one agent that specifically or selectively binds to IL17 is labeled directly with a secondary antibody.

* * * * *